United States Patent
Lamer et al.

(10) Patent No.: US 7,349,859 B1
(45) Date of Patent: Mar. 25, 2008

(54) DATA MANAGEMENT SYSTEM FOR PATIENT DATA

(75) Inventors: Roland Lamer, Evanston, IL (US); Theodore Anagnost, Skokie, IL (US)

(73) Assignee: The General Electric Company, Schenectady, NY (US)

( * ) Notice: Subject to any disclaimer, the term of this patent is extended or adjusted under 35 U.S.C. 154(b) by 0 days.

(21) Appl. No.: 09/543,663

(22) Filed: Apr. 5, 2000

Related U.S. Application Data

(63) Continuation-in-part of application No. 09/474,569, filed on Dec. 29, 1999.

(51) Int. Cl.
*A61B 5/00* (2006.01)

(52) U.S. Cl. .......................................... 705/3; 707/102

(58) Field of Classification Search ............... 705/2–3; 707/104, 102, 10
See application file for complete search history.

(56) References Cited

U.S. PATENT DOCUMENTS

| | | | | |
|---|---|---|---|---|
| 5,581,460 A | * | 12/1996 | Kotake et al. | 705/3 |
| 5,586,262 A | * | 12/1996 | Komatsu et al. | 705/2 |
| 5,668,998 A | * | 9/1997 | Mason et al. | 706/924 |
| 5,710,889 A | | 1/1998 | Clark et al. | 395/244 |
| 5,772,585 A | * | 6/1998 | Lavin et al. | 600/300 |
| 5,924,074 A | | 7/1999 | Evans | 705/3 |
| 6,260,021 B1 | * | 7/2001 | Wong et al. | 705/1 |
| 6,266,675 B1 | * | 7/2001 | Evans et al. | 707/104.1 |
| 6,314,415 B1 | * | 11/2001 | Mukherjee | 706/47 |
| 6,363,393 B1 | * | 3/2002 | Ribitzky | 707/102 |
| 6,574,629 B1 | * | 6/2003 | Cooke et al. | 707/10 |
| 6,779,024 B2 | * | 8/2004 | DeLaHuerga | 709/217 |
| 2001/0041991 A1 | * | 11/2001 | Segal et al. | 705/3 |
| 2003/0229514 A2 | * | 12/2003 | Brown | 705/2 |

\* cited by examiner

*Primary Examiner*—Andrew Joseph Rudy
*Assistant Examiner*—Vanel Frenel
(74) *Attorney, Agent, or Firm*—Andrus, Sceales, Starke & Sawall, LLP

(57) ABSTRACT

According to an exemplary embodiment, a data management system for patient data includes a first component, a second component, and a container application. The first component has a functionality code segment and a user interface code segment. The second component has a functionality code segment and a user interface code segment. The container application has a first user interface layer in communication with the first component and a second user interface layer in communication with the second component. The first and second user interface layers are configured to communicate patient data between the functionality code segments of the first and second components, respectively, and a user interface.

19 Claims, 8 Drawing Sheets

DATA MANAGEMENT SYSTEM FOR PATIENT DATA

This application is a continuation-in-part of commonly assigned U.S. application Ser. No. 09/474,569, filed Dec. 29, 1999, entitled "PATIENT DATA INFORMATION SYSTEM" to Lamer et al.

FIELD OF THE INVENTION

This invention relates to data management systems, and more particularly to a patient data management system to integrate first and second patient data systems.

BACKGROUND OF THE INVENTION

Medical scanners and medical imaging machines are an integral part of modern medical practice. The scanners and medical imaging devices utilize both electromagnetic radiation and sonic wave to produce images which are viewed by doctors for the diagnosis and care of patients. For example, ultrasound machines are useful for viewing fetuses during prenatal care in a pregnancy or blood flow patterns in arteries. Magnetic resonant imaging machines are useful for producing images in a wide variety of soft tissues. Computer tomology imaging machines are useful for producing images of scalable structures.

In a hospital, medical scanners and medical imaging devices are preferably networked with a central image management system such as a Picture Archival and Communications System (PACS). The PACS is designed to provide a central storage for archive of medical images. Further, PACS is configured so that stored images may be retrieved. Typically, a hospital will have a single PACS that is networked with a plurality of medical scanners and medical imaging devices located throughout the hospital. Further, the PACS will be networked with a plurality of image workstations, such as a PACS workstation. Images generated by medical scanners and medical imaging devices are transferred to the PACS for storage and later retrieval and review by doctors located throughout the hospital at any of the plurality of image workstations.

Also in a hospital, medical scanners and medical imaging devices are coupled to a Radiology Information System (RIS). The RIS is designed to provide a central storage for archive of patient textual data as well as information relating to the medical procedures, reports, medical orders, test results, patient demographics, etc. Further, RIS is configured so that stored textual information may be retrieved by a user. Typically, a hospital will have a single RIS that is networked with a plurality of workstations located throughout the hospital. Patient information generated at these workstations by users, such as radiology technicians, nurses, radiologists, and physicians, are transferred to the RIS for storage and later retrieval and review by radiologists located throughout the hospital at any of the plurality of RIS workstations.

A conventional PACS system and a RIS system, as explained above, are completely separate and distinct systems. Each system duplicates many of the components in each system thereby increasing the capital expenditure costs and maintenance expenses incurred by the hospital. Typically, an information exchange bridge referred to as a PACS broker, which links the two systems, can be used, but a radiologist must still access image data from the separate PACS workstation and patient textual data from the separate RIS workstation. In other words, the radiologist must have two separate workstations readily available in order to review patient images and patient textual data to completely diagnose a patient.

Thus, there is a need for a patient data information system that integrates the patient image data and patient textual data on a single workstation. There is a further need for a patient data information system that allows the user to access patient image data and patient textual data, manipulate such data as is necessary for treatment and enter new data concerning such patient treatment in a single workstation. In addition, there is a need for a patient information system that is accessible by a plurality of users that can retrieve and input data, either textual data or image data, simultaneously. Further still, there is a need for a single point of contact application where RIS and PACS functionality are seamlessly integrated, where data is shared, and where a user receives a consistent user interface.

SUMMARY OF THE INVENTION

According to an exemplary embodiment, a data management system for patient data includes a first component, a second component, and a container application. The first component has a functionality code segment and a user interface code segment. The second component has a functionality code segment and a user interface code segment. The container application has a first user interface layer in communication with the first component and a second user interface layer in communication with the second component. The first and second user interface layers are configured to communicate patient data between the functionality code segments of the first and second components, respectively, and a user interface.

According to another exemplary embodiment, a data management system for patient data includes a first application, a second application, and a data manager. The first application retrieves patient image data from a data base. The second application processes patient text data. The data manager is in communication with the first and second applications, and includes a user interface code segment in communication with the first and second applications for receiving the patient image data and patient text data and for generating display signals based on the patient image data and the patient text data according to a predetermined display format.

According to yet another exemplary embodiment, a data management system for patient data includes a first component, a second component, a first service layer, a second service layer, and a service. The first component is configured to retrieve patient image data. The second component has a second functionality. The first service layer is configured to communicate with the first component. The second service layer is configured to communicate with the second component. The service is configured to communicate with the first component and the second component via the first and second service layers, respectively. The service communicates with the first and second components via a predetermined protocol.

According to still another exemplary embodiment, a data management system for patient data includes a first means for processing patient image data, a second means for processing patient text data, and a third means for communicating between the first and second means. The third means receives patient image data and patient text data from the first and second means, and displays the patient image data and patient text data according to a predetermined display format.

According to still another exemplary embodiment, a method of displaying patient data from a plurality of applications includes: receiving patient image data, receiving patient text data, configuring both the patient image data and patient text data according to a predetermined display format, and displaying the configured patient image data and patient text data.

DETAILED DESCRIPTION OF THE PREFERRED EMBODIMENTS

Figure 1:
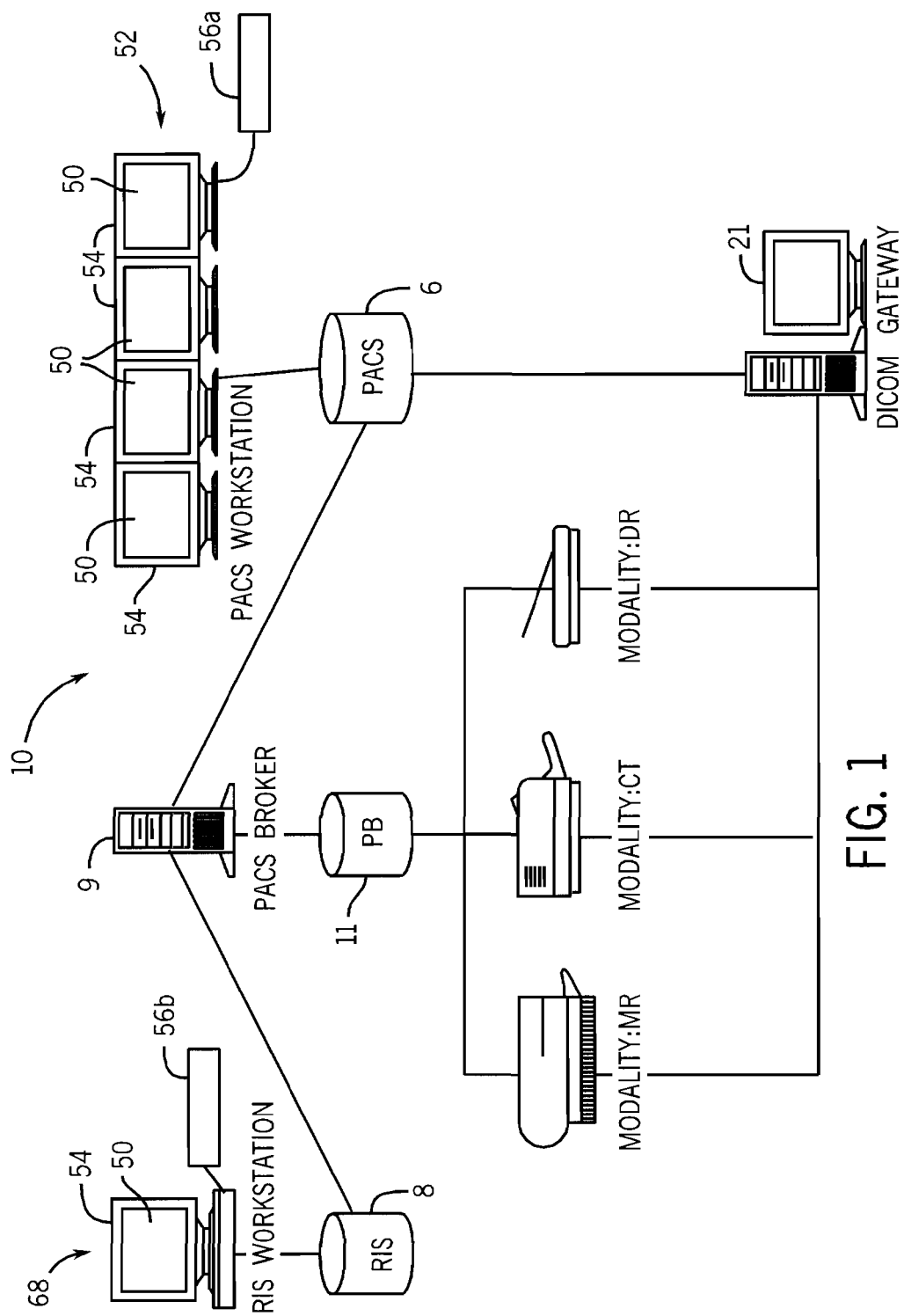
FIG. 1 is an illustration of a PACS workstation and its associated data base containing a patient data information system according to an exemplary embodiment interconnected through a PACS broker to a RIS workstation and its associated data base with a plurality of modality types providing patient image and textual data to the respective RIS and PACS databases through the PACS broker in a DICOM gateway.

Referring to FIG. 1, there is illustrated an exemplary embodiment of a patient data information system (10). A workstation (52) has a display unit (50), which can include a plurality of monitors (54), coupled to a Picture Archival and Communication System (PACS) and associated PACS data base (6). The data base (6) associated with workstation (52) is in communication with a PACS broker (9) which allows communication between the data base of workstation (52) and a second data base (8) associated with a second workstation (68) and provides access to a Radiology Information System (RIS) and its associated RIS data base (8). The workstations (52) and (68) are each provided with an input unit (56a, 56b). The input units (56a, 56b) can include one or more of a mouse, a voice recognition system, a keyboard keystroke assembly, a switch, and a light pen for inputting and retrieving information from the respective workstation.

Figure 2:
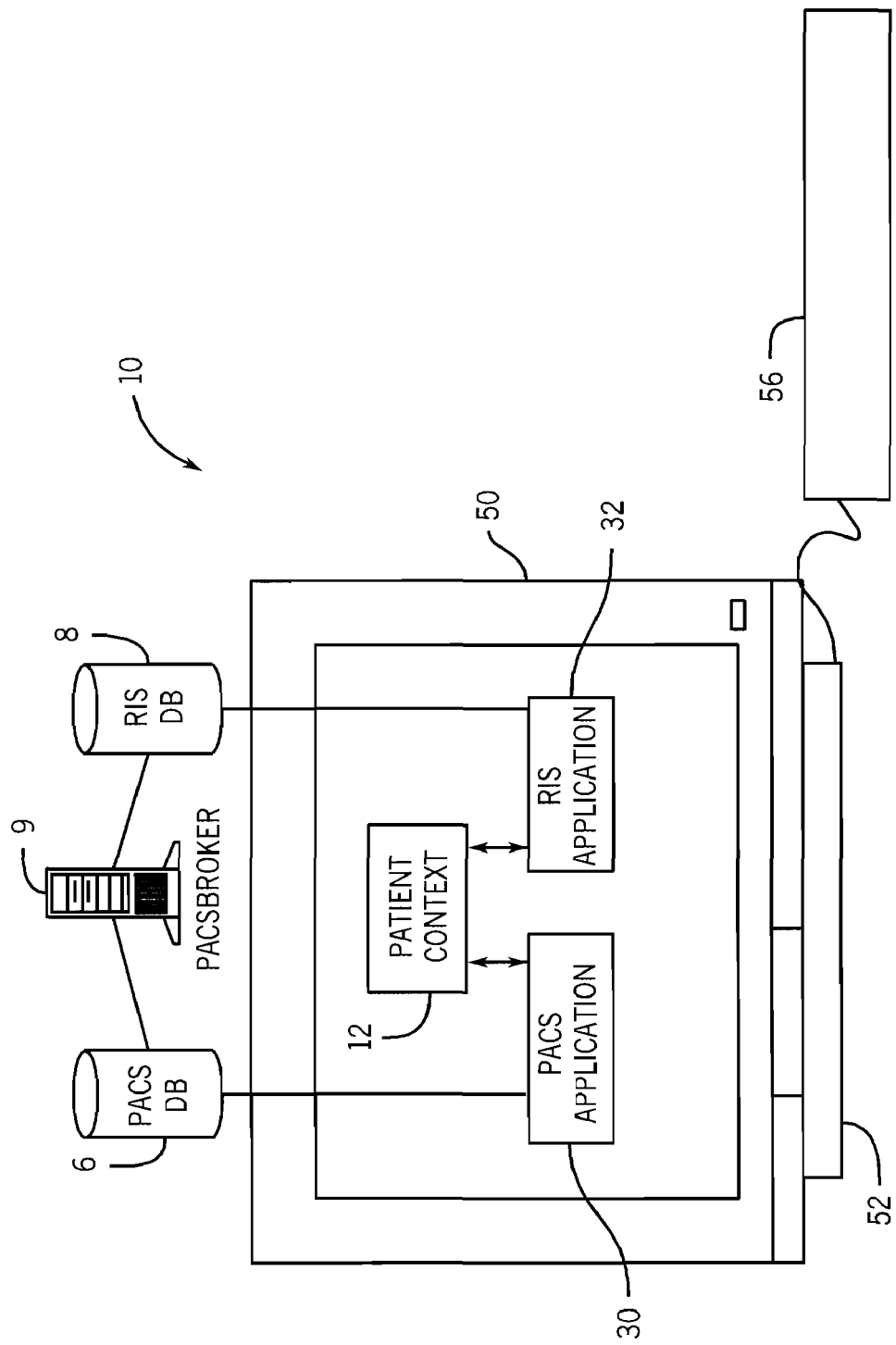
FIG. 2 is an illustration of the PACS workstation displaying PACS application information on the workstation monitor together with RIS application information displayed on the same monitor with a patient context being transmitted from one application to another in the background, according to an exemplary embodiment.

The patient data information system (10) provides for integration between the applications residing on workstation (52) and third party applications residing on the same workstation or the network to which the workstation is coupled to improve work flow and productivity of patient data information. During the treatment of a patient, a user, typically a radiologist, will log on to a workstation to obtain patient information, usually textual data as well as image data. The user will manipulate or use that information and provide additional input based on observation and analysis relating to the treatment and care of the patient based on the patient data (14) (FIG. 4) made available on information system (10). The present patient data information system (10) integrates the patient image data (16) (FIG. 6) with the patient textual data (18) on the same workstation. The present patient data information system (10) provides the communication mechanism that allows different applications residing on the workstation or on the network to which the workstation is attached to share context information. System (10) includes a conduit that allows two-way patient context exchanges between the multiple applications residing on the same workstation or the same workstation network. The patient context (12) (FIG. 2) includes, for example, patient identification data, user identification data, patient examination information, etc. Patient data (14) is obtained by inputting data, either textual data (18) or image data (16) from the various modalities to which a patient is subjected during a medical examination. Such modalities can include magnetic resonance imaging (MRI) devices or ultrasound or computer tomology imaging (CT) devices or it can include data inputted with a word processing application. Such patient data (14) is stored in either the RIS data base (8) or the PACS data base (6) either directly through PACS broker data base (11) or through a DICOM gateway (21).

The present patient data information system (10) comprises a display unit (50) which can include one or more high resolution monitors (54) coupled to a workstation (52). The workstation (52) is configured to operate a first software application (30) configured to display patient images (16), for a patient, on display unit (50) upon request by a user via an input unit (56a) coupled to workstation (52). The first application (30) (FIG. 2) is configured to generate a patient context (12) for the patient and provide the patient context (12) to a second software application (32). The second application (32) displays patient data (14) from the second application (32) based on the patient context (12). In this exemplary embodiment, the first application (30) is configured to retrieve patient image data (16) from a Picture Archival and Communication System (PACS) database (6) and the second application (32) is configured to retrieve patient textual data (18) from a Radiology Information System (RIS) database (8) wherein the patient data (14) includes the patient textual data (18). As is mentioned above, the display unit (50) includes a monitor (54) having a resolution of at least 90 dots per inch (dpi), though displays having other resolutions are contemplated.

During the process of operating the patient data information system (10) the second application (32) is, for example, an RIS application, such as, a case sign out application, a report entry application, an order detailing application, an order viewer application, etc. Such applications are invoked by activating a command such as by "clicking" on an icon displayed in a graphic user interface on the monitor (54) of the display unit (50) of the workstation (52) as determined by the user of the patient data information system (10). The procedure can also be invoked by the user utilizing an input unit (56a), for example, a mouse, a voice recognition system, a keyboard keystroke, a switch, and a light pen, etc.

Upon logging onto the workstation (52) or at another time during operation of system (10), a patient context (12) is created. The patient context (12) includes patient identification data such as name, address, age, social security number, etc., associated with a specific and particular patient. The patient context (12) can also include user identification data such as the name, password, etc., of the user of the patient data information system (10). In addition, the patient context (12) can also include patient examination information relating to that specific and particular patient, such as, ordered tests, test results, test analysis, prognosis, diagnostic information, etc. The first application (30) shares the patient context (12) with the second application (32). In the exemplary embodiment, the first application (30) is in communication with the PACS data base (6) and the second application (32) is in communication with the RIS data base (8), which databases (6, 8) are interconnected to the PACS broker (9).

Figure 3:
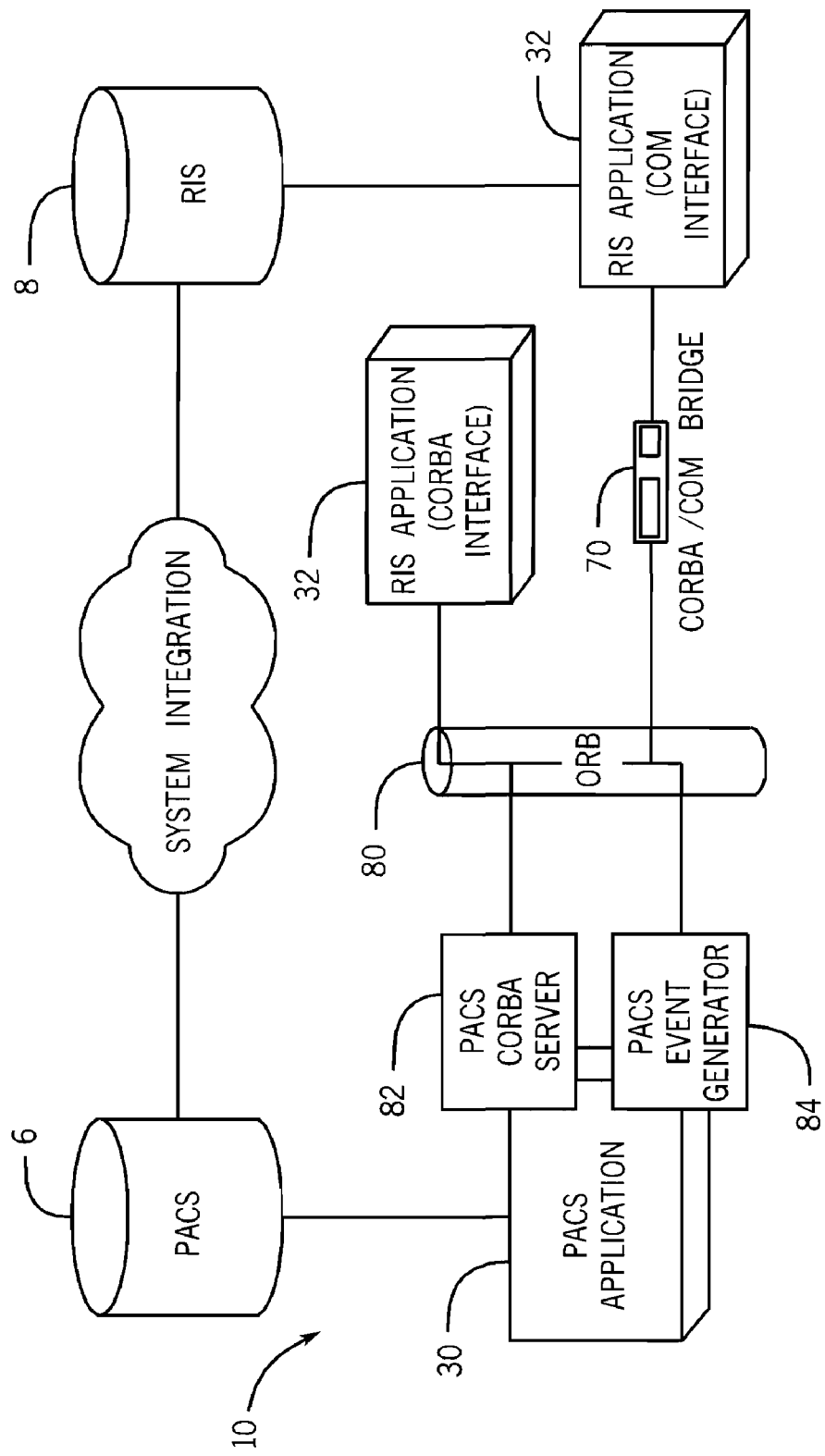
FIG. 3 is a block diagram illustrating the patient information data system architecture according to an exemplary embodiment.

Referring to FIGS. 1 and 3, another embodiment of the patient data information system (10) includes a second workstation (68) coupled to the workstation (52) with the second workstation (68) configured to operate the second application (32). An object request broker (80) allows the software application on one workstation to communicate with another software application operating on the second workstation or to communicate with two applications on the same workstation. To further facilitate the communication between two applications, a bridge (70) is coupled between the second workstation (68) and the object request broker (80), wherein the second application (32) operating on the second workstation (68) communicates with the first application (30) operating on the first workstation (52) via a Component Object Model (COM). The Component Object Model is a Microsoft Corporation specification which is binary compatible with a C++ compiler v-table generator which facilitates basic C++ classes. In operation, the first application (30) preferably is accessing and manipulating patient image data via PACS database (6). A CORBA server (82) is a CORBA-based interface to allow the first application (30) to interface and communicate with other applications operating on the system. CORBA is a common object request broker architecture specification adopted by software developers that uses an object orientated approach to create reusable software components. The CORBA server (82) creates an object in accordance with the specification and upon which operations can be invoked by the first application. The objects created by the CORBA server (82) correspond to certain actions that can be performed by the first application (30). In an event generator (84) operated with the first application is an event suite that is used to send notification of what the first application (30) is currently or has finished processing. The common object request broker architecture is used to implement the communication layer between the several applications operating on the patient data information system (10). The common object request broker architecture provides an infrastructure that enables invocations of operations on objects created by the CORBA located anywhere on the network to which the workstation (52) is connected as if that object was on the local workstation (52). The object request broker (80) facilitates the communication between the first application (30) and the second application (32). If the second application (32), typically configured for processing the patient textual data (18) of a RIS data base (8), is created by CORBA, a direct communication with the second application is available through the object request broker (80). If the patient textual data (18) on the RIS data base (8) is created by the component object model, a bridge (70) must then be invoked to translate between the component object model and the common object request broker architecture. This COM/CORBA bridge allows bidirectional messaging between objects written using CORBA and those written using COM. The bridge does the conversion between the two distributed objects in a seamless manner from the point-of-view of the user of the patient data information system (10).

Figure 4:
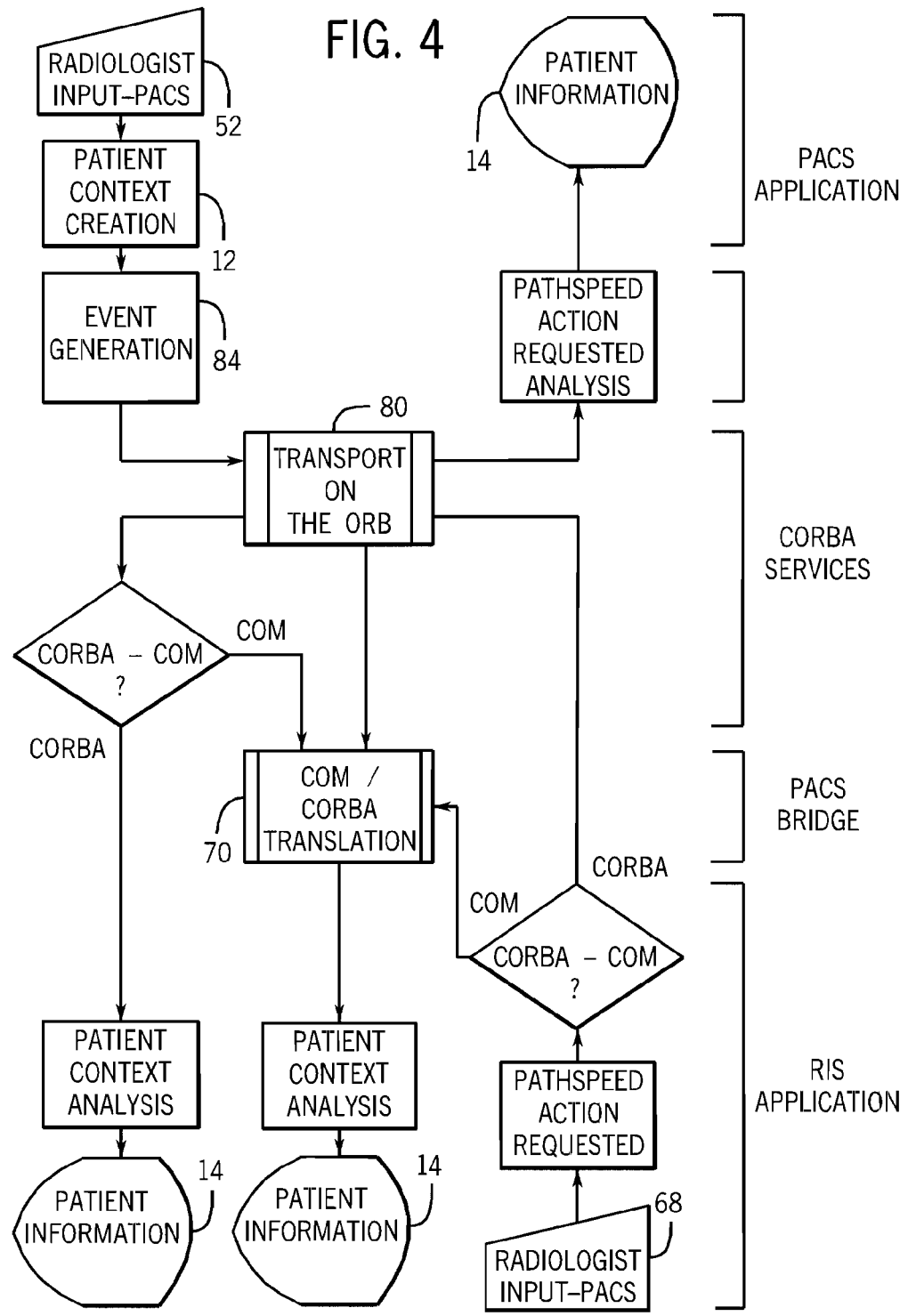
FIG. 4 is a flow chart illustrating the process flow of the patient data information system according to an exemplary embodiment.

Referring to FIG. 4, there is shown a flow chart of the integration process of the present patient data information system (10). A user logs onto the system at either the PACS workstation (52) or the RIS workstation (68) utilizing a user interface displayed on the monitor (54) of the display unit (50) of the workstation. Upon such login, a patient context (12) is created. The patient context (12) object is wrapped into an event by the event generator (84) and sent to the second application (32), typically the RIS application, via the object request broker (80). If the RIS application is CORBA-enabled it will receive and analyze the event and display the pertinent patient information based on the received patient context (12). If the RIS application is COM enabled, the event is translated from COM to CORBA using the bridge (70). A similar procedure is provided if the initiating logon occurs at a RIS workstation (68).

Figure 5:
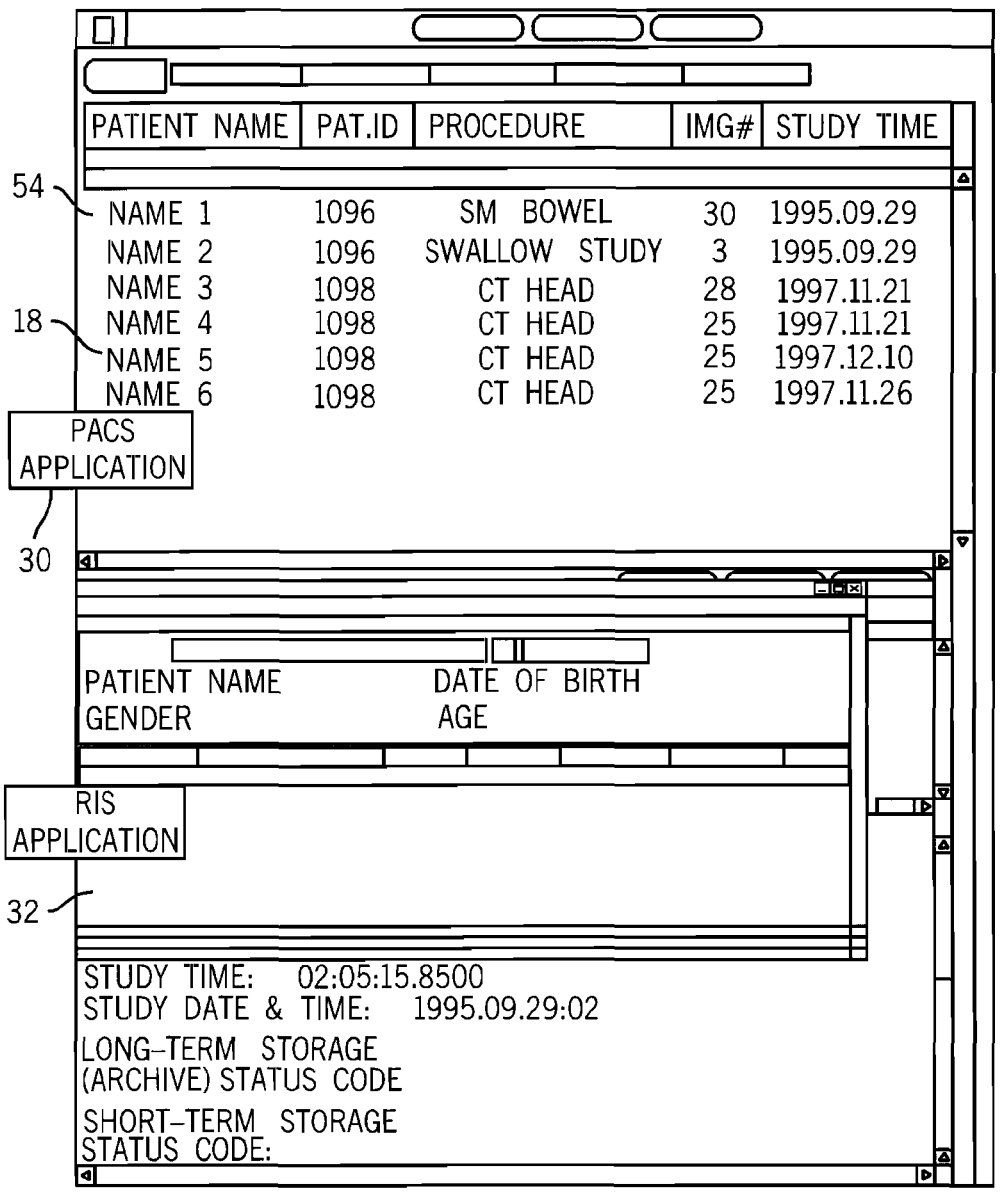
FIG. 5 is an example of an annotated window of the monitor of the PACS workstation displaying patient data according to an exemplary embodiment.

FIG. 5 is an example of a monitor screen on a workstation in the present patient data information system (10) displaying patient textual data (18) from a first application (30) and patient textual data (18) from a second application (32). The first application (30) in the illustration is from a PACS data base (6) and the second application (32) data is from a RIS data base (8).

Figure 6:
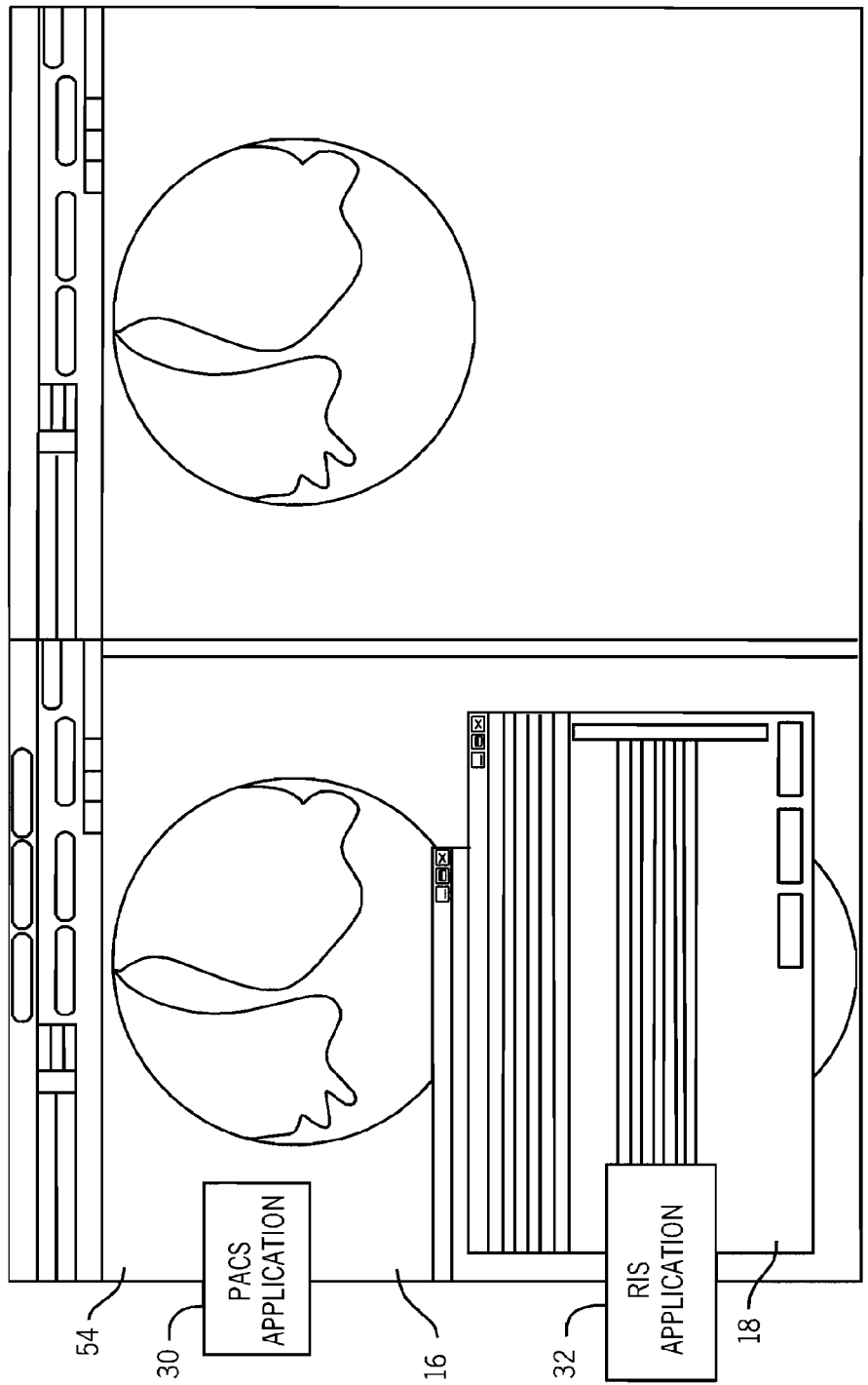
FIG. 6 is an example of an annotated window of the patient data information system displaying patient image data and patient textual data according to an exemplary embodiment.

FIG. 6 is an example of a screen on a monitor (54) of a workstation display unit (50). The first application (30) is displaying patient image data (16) and the second application (32) is displaying patient textual data (18).

Figure 7:
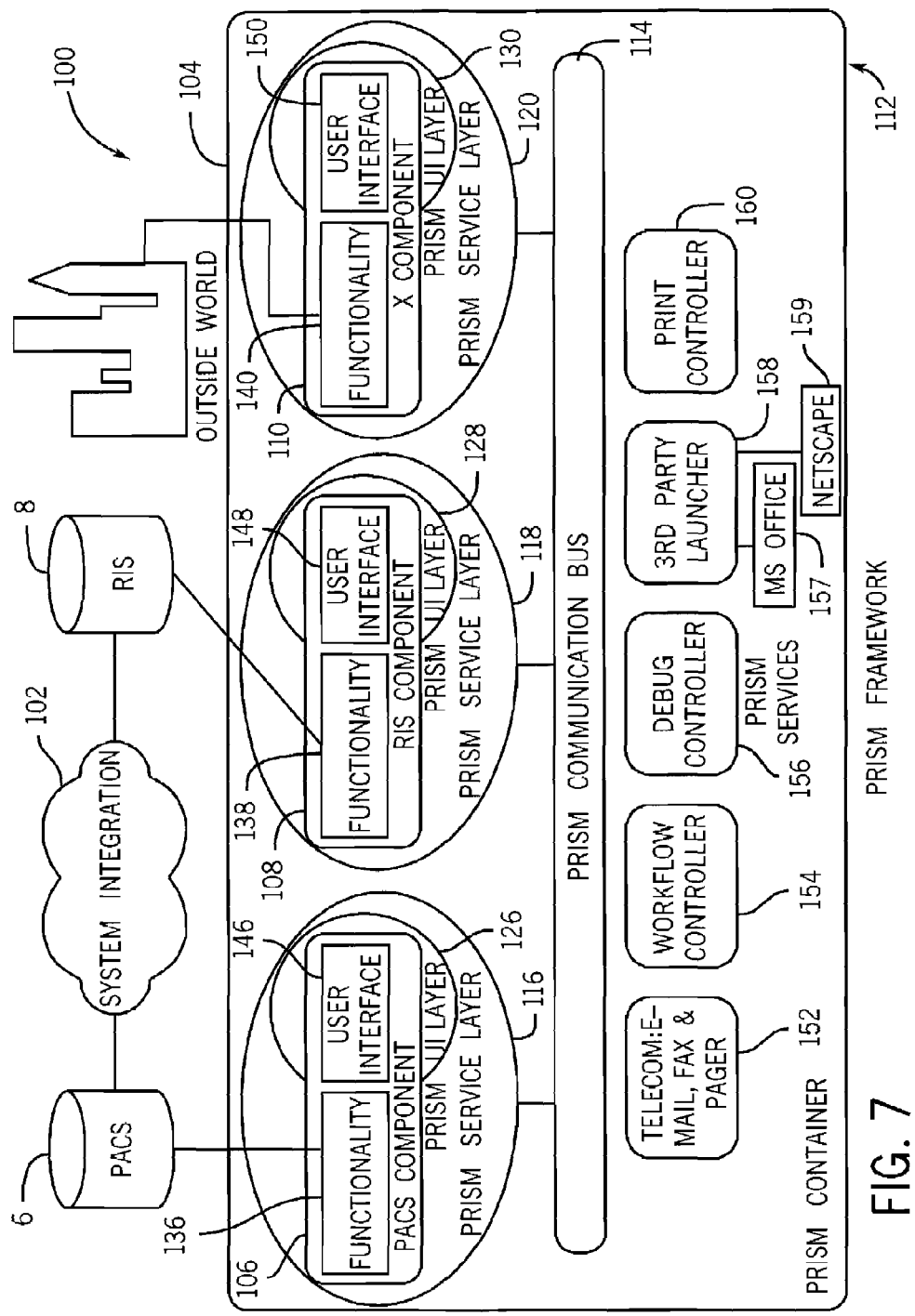
FIG. 7 is a diagram of a data management system for patient data disclosing a further improvement on the system disclosed with reference to FIGS. 1-4.

Referring now to FIG. 7, a diagram of a data management system (100) for patient data is shown. System (100) is a further improvement on the system disclosed with reference to FIGS. 1-4. System (100) includes PACS data base (6) and RIS data base (8) coupled to one another by a system integration (102), as is shown in FIG. 1. System (100) further includes a PACS RIS Integrated Software Manager (PRISM) container (104). Container (104) is an application operable on PACS workstation (52), RIS workstation (68), some combination thereof, or some other computer system. Container (104) integrates the functionality of a PACS application or component (106), a RIS application or component (108), and another application or component (110) (i.e., identified as "X component"), though as few as two components and many more than three components may be implemented.

Container (104) includes services (112), a communication bus (114), service layers (116, 118, 120), and user interface layers (126, 128, 130). The architecture of container (104) is based on componentware and the component model used is Java Beans, though other component models may be used (e.g., Distributed Component Object Model (DCOM), Common Object Request Broker Architecture (CORBA), etc.). Component architecture is a notion in object-oriented programming where "components", or objects, of a program are completely generic. Instead of having a specialized set of methods and fields they have generic methods through which the component can advertise the functionality it supports to the system into which it is loaded. This enables completely dynamic loading of objects.

Service layers (116, 118, 120) and user interface layers (126, 128, 130) are "layers", in this exemplary embodiment.

Examples of layered protocols are TCP/IP's five layer protocol stack and the OSI seven layer model. A layer, or protocol layer, is a software and/or hardware environment of two or more communications devices or computers in which a particular network protocol operates. A network connection may be thought of as a set of more or less independent protocols, each in a different layer or level. The lowest layer governs direct host-to-host communication between the hardware at different hosts; the highest layer consists of user application programs. Each layer uses the layer beneath it and provides a service for the layer above. Each networking component, hardware or software, on one host uses protocols appropriate to its layer to communicate with the corresponding component on another host.

The advantages of layered protocols is that the methods of passing information from one layer to another are specified clearly as part of the protocol suite, and changes within a protocol layer are prevented from affecting the other layers. This greatly simplifies the task of designing and maintaining communication systems.

Container (104) is configured to create, assemble and manage the plurality of components (106, 108, and 110) within container (104) during runtime. When container (104) is started, container (104) is configured to create components (106, 108, and 110). Components (106, 108, and 110) each include a respective functionality (136, 138, and 140) and user interface (146, 148, and 150). Functionalities (136, 138, and 140) are code segments or programs which are configured to perform certain tasks. For example, functionality (136) is configured to store and retrieve patient image data from PACS database (6). Functionality (138) is configured to store and retrieve patient text data from RIS database (8). Functionality (140) is configured to communicate with the outside world (e.g., an internet, intranet, or other system). Functionality (140) could include voice recognition, MS-OUTLOOK, database management, etc.

User interfaces (146, 148, and 150) include code segments or programs which receive user input and/or generate display signals for a user display, such as displays (50) (FIG. 1). Typically, user interfaces (146, 148, and 150) are configured by different companies or programmers, such that the look and feel of these user interfaces is not consistent. "Look and feel" refers to appearance and function of a program's user interface, and is a term most often applied to graphical user interfaces (GUI) but might also be used by extension for a textual command language used to control a program. Look and feel includes such things as the icons used to represent certain functions such as opening and closing files, directories and application programs and changing the size and position of windows; conventions for the meaning of different buttons on a mouse and keys on the keyboard; and the appearance and operation of menus. A user interface with a consistent look and feel is considered by many to be an important factor in the ease of use of a computer system.

According to one advantageous aspect of container (104), PRISM user interface layers (126, 128, and 130) control user interfaces (146, 148, and 150) by plugging in a predetermined display format, such as a predetermined look and feel. User interface layers (126, 128, and 130) include code segments or programs configured to convert the customized user interface aspects of components (106, 108, and 110) to a uniform user interface format. Therefore, a user sees a uniform user interface format on display (50) when interfacing with any of PACS component (106), RIS component (108), and X component (110).

Container (104) further includes a system for allowing communication among components (106, 108, and 110) and communication between each component and various services. A service layer (116, 118, and 120) is in communication with each of components (106, 108, and 110), respectively. Service layers (116, 118, and 120) include code segments or other programs configured to convert data from a protocol usable by components (106, 108, and 110) to a uniform predetermined protocol usable via communication bus (114), such as, Java Beans, CORBA, DCOM, etc. Components (106, 108, and 110) are configured to access various services (112) via the respective service layers (116, 118, and 120) and via communication bus (114). Services (112) include, for example, a telecommunication service (152) having such features as e-mail, facsimile, and pager; a workflow controller (154) for establishing macros or other tasks for individual users or groups of users (e.g., Radiologists, Transcriptionists, etc.); a debug control for surveillance and diagnostics of the services; a third party launcher which provides a user interface for launching other applications, such as MS-OFFICE (157) and NETSCAPE (159); and a print controller for providing printing services for various printers. Services (112) may comprise fewer than those listed, or additional services.

Figure 8:
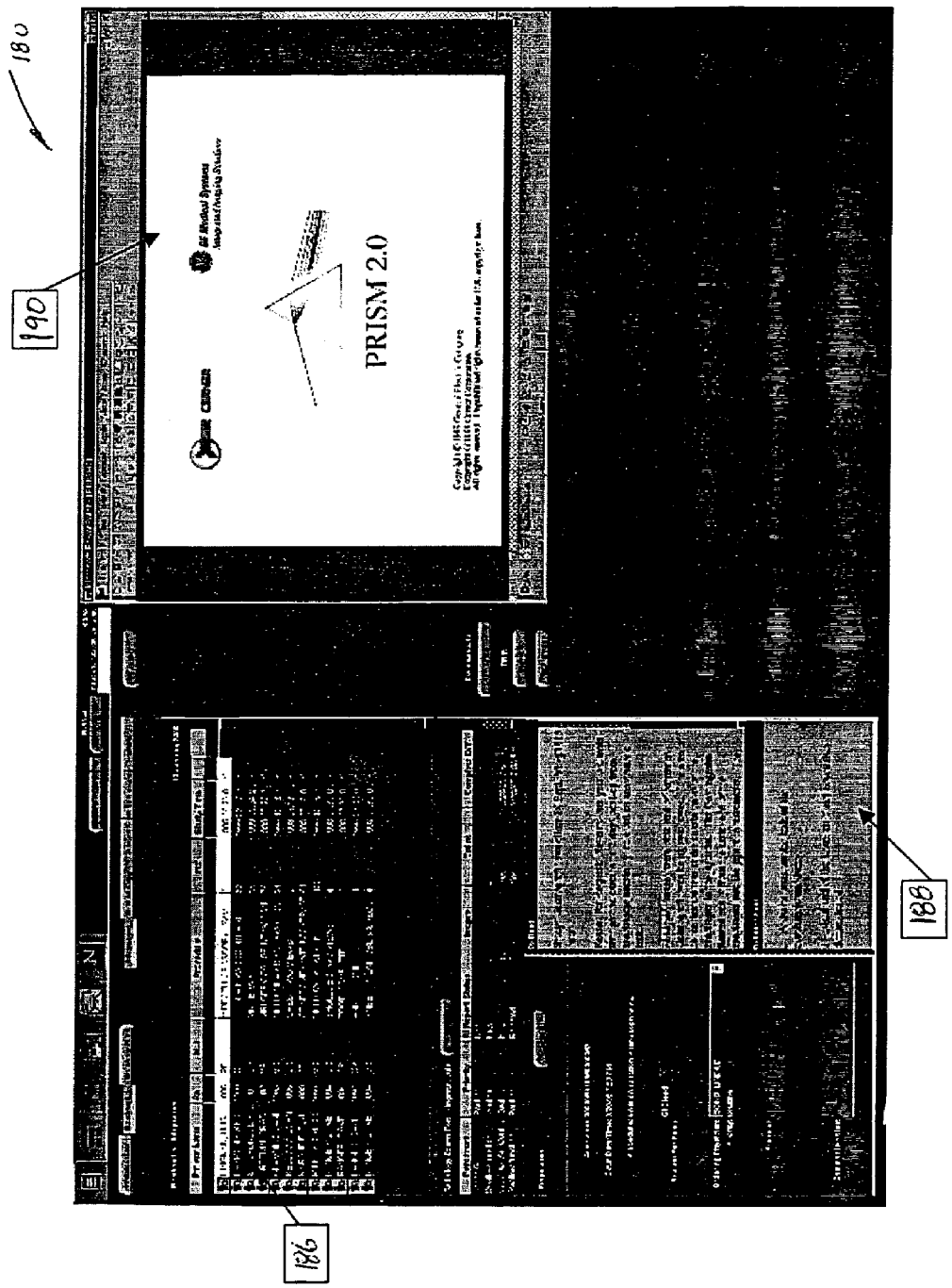
FIG. 8 is an example of an annotated window of a monitor displaying patient data according to the data management system of FIG. 7.

Referring now to FIG. 8, a monitor screen (180) on a workstation (52) is shown. Screen (180) shows the user interface output of system (100) using container (104). Through user interface layers (126 and 128), components (106 and 108) interface with the user at portions (186 and 188) of screen (180). It can be seen that portions (186 and 188) have a similar look and feel based on the predetermined display format. The use of PACS component (106) and RIS component (108) is greatly simplified to the user with this improvement. A further portion 190 of screen 180 illustrates a view generated by third party launcher 158 which has launched a Microsoft PowerPoint application.

Thus, there is provided a patient data information system that integrates patient data including patient image data and patient textual data in a patient context on a single workstation. While several embodiments of the present invention have been disclosed and described in detail herein, various modifications may be made. For example, the exemplary embodiment of the patient data information system was described in a Microsoft Corporation Windows NT environment. Other networking operating systems can also be used to integrate the patient image data and patient textual data in a seamless fashion on a single workstation. By way of further modification, the communication between workstations, the PACS broker and the PACS and RIS data bases, can be facilitated by a wireless communication system or by an optical link communication system. The invention is not limited to a particular embodiment, but extends to various modifications that nevertheless fall within the scope of the appended claims.

What is claimed is:

1. A data management system for patient data, comprising:

a picture archival and communication system (PACS) having a functionality code segment and a first user interface code segment;

a radiology information system (RIS) having a functionality code segment and a second user interface code segment;

a container application having a first user interface layer in communication with the PACS and a second user interface layer in communication with the RIS, wherein the first and second user interface layers are configured to convert the first user interface code segment of the PACS and the second user interface code segment of the RIS to a uniform user interface and communicate patient data between the functionality code segments of the PACS and the RIS, respectively, and the uniform user interface such that the patient data of the functionality code segments of the PACS and the RIS are formatted in a common protocol; and further wherein each of the PACS and the RIS include a workstation configured such that patient data can be communicated between the PACS and RIS workstations through the container application.

2. The data management system of claim 1, wherein the functionality code segment of the PACS is configured to store and retrieve patient image data.

3. The data management system of claim 2, wherein the functionality code segment of the RIS is configured to store and retrieve patient text data.

4. The data management system of claim 1, the container further comprising a first service layer in communication with the PACS and a second service layer in communication with the RIS, wherein the first and second service layers are configured to communicate data between the functionality code segments of the PACS and the RIS and a service.

5. The data management system of claim 4, wherein the service includes a telecommunication service.

6. The data management system of claim 4, wherein the service communicates with the first and second layers via a predetermined protocol.

7. The data management system of claim 6, wherein the predetermined protocol includes componentware.

8. The data management system of claim 1, further comprising a third component having a functionally code segment and a third user interface code segment, wherein the container application is configured to communicate patient data between the functionality code segments of the PACS, RIS and third components, respectively, and the uniform user interface.

9. The data management system of claim 8, wherein the functionality code segment of the third component is configured to communicate with the Internet.

10. A data management system for patient data, comprising:
   a picture archival and communication system (PACS) for retrieving patient image data from a database and having a first user interface;
   a radiology information system (RIS) for processing patient text data and having a second user interface;
   a data manager in communication with the PACS and the RIS, wherein the data manager includes a user interface code segment in communication with the PACS and the RIS for converting the first user interface and the second user interface to a uniform user interface for receiving the patient image data and patient text data for generating display signals based on the patient image data and the patient text data for generating display signals based on the patient image data and the patient text data according to a predetermined display format, wherein the predetermined display format includes a common protocol for the patient image data and the patient text data; and
   further wherein each of the PACS and the RIS include a workstation configured such that patient data can be communicated between the PACS and RIS workstations through the data manager.

11. The data management of claim 10, further comprising a display unit configured to receive the display signals and provide a display based on the display signals.

12. The data management system of claim 10, fixer comprising a third application configured to process data, the user interface code segment in communication with the third application and configured to receive the data and to generate display signals based on the data.

13. The data management system of claim 12, wherein the third application is in communication with the internet.

14. A method of displaying patient data from a plurality of applications, comprising:
   receiving patient image data using a picture archival and communication system (PACS) having a first user interface;
   receiving patient text data using a radiology information system (RIS) having a second user interface;
   converting the first user interface and the second user interface to a uniform user interface;
   configuring both the patient image data and patient text data according to a predetermined display format;
   displaying the configured patient image data and patient text data on the uniform user interface according to the display format such that the patient image data and the patient text data have the a common protocol; and
   communicating the configured patient image data and patient text data between the first user interface workstation and the second user interface through a container application when a user is not utilizing the uniform user interface.

15. The method of claim 14, further comprising receiving the patient image data from a PACS data base.

16. The method of claim 14, wherein the predetermined display format includes a display format for an icon.

17. The method of claim 14, wherein the predetermined display format includes a display format for a menu.

18. The method of claim 14, further comprising providing patient image data to one of the internet and an intranet.

19. The method of claim 14, further comprising providing patient image data to one of the internet and an intranet.

* * * * *